(12) United States Patent
Ueno et al.

(10) Patent No.: US 6,923,015 B2
(45) Date of Patent: Aug. 2, 2005

(54) REFRIGERATOR

(75) Inventors: Shunji Ueno, Osaka (JP); Susumu Saruta, Osaka (JP); Katsushi Sumihiro, Osaka (JP)

(73) Assignees: Kabushiki Kaisha Toshiba, Tokyo (JP); Toshiba Ha Products Co., Ltd., Osaka (JP); Toshiba Consumer Marketing Corporation, Tokyo (JP)

( * ) Notice: Subject to any disclaimer, the term of this patent is extended or adjusted under 35 U.S.C. 154(b) by 0 days.

(21) Appl. No.: 10/490,892

(22) PCT Filed: Sep. 24, 2002

(86) PCT No.: PCT/JP02/09812

§ 371 (c)(1),
(2), (4) Date: Mar. 26, 2004

(87) PCT Pub. No.: WO03/029733

PCT Pub. Date: Apr. 10, 2003

(65) Prior Publication Data

US 2004/0237544 A1 Dec. 2, 2004

(30) Foreign Application Priority Data

Sep. 28, 2001 (JP) ........................................ 2001-303767

(51) Int. Cl.[7] .............................................. F25D 23/00
(52) U.S. Cl. ............................. 62/264; 62/78; 422/121
(58) Field of Search ........................... 62/78, 264, 440, 62/441, 443; 422/120, 121, 122, 123

(56) References Cited

U.S. PATENT DOCUMENTS

| | | | | |
|---|---|---|---|---|
| 4,904,289 A | * | 2/1990 | Miyakami et al. | 62/157 |
| 4,948,567 A | * | 8/1990 | Atarashiya | 422/122 |
| 5,078,971 A | * | 1/1992 | Matuda et al. | 422/121 |
| 5,087,426 A | * | 2/1992 | Inoue et al. | 422/123 |
| 5,250,265 A | * | 10/1993 | Kawaguchi et al. | 422/107 |
| 5,347,820 A | * | 9/1994 | In Gweon | 62/78 |
| 5,501,084 A | * | 3/1996 | Chang et al. | 62/264 |
| 5,601,786 A | * | 2/1997 | Monagan | 422/108 |
| 5,958,346 A | * | 9/1999 | Evans, Jr. | 422/120 |
| 6,134,806 A | * | 10/2000 | Dhaemers | 34/404 |
| 6,227,458 B1 | * | 5/2001 | Dever et al. | 239/36 |
| 6,515,422 B1 | * | 2/2003 | Honda | 313/635 |
| 6,613,277 B1 | * | 9/2003 | Monagan | 422/24 |
| 2002/0037240 A1 | | 3/2002 | Okada et al. | |

FOREIGN PATENT DOCUMENTS

| | | |
|---|---|---|
| DE | 92 15 919.2 | 4/1993 |
| EP | 0 325 133 A1 | 7/1989 |
| EP | 0 577 251 A1 | 1/1994 |
| EP | 0 719 995 A2 | 7/1996 |
| EP | 0 769 322 A | 4/1997 |
| JP | 401067584 A * | 3/1989 |
| JP | 404020773 A * | 1/1992 |
| JP | 6-15143 | 1/1994 |
| JP | 0 687 874 A1 | 12/1995 |
| JP | 2000-432 | 1/2000 |
| JP | 02001263916 A * | 9/2001 |

* cited by examiner

Primary Examiner—Harry B. Tanner
Assistant Examiner—Mohammad M. Ali
(74) Attorney, Agent, or Firm—Pillsbury Winthrop Shaw Pittman

(57) ABSTRACT

A refrigerator includes a refrigerating cycle unit for refrigerating an atmosphere in the refrigerator by means of heat absorption due to change of a flammable refrigerant from a liquid phase to a gaseous phase, and a deodorizer having first and second electrodes discharging electricity upon application of high voltage to them, producing ozone, a burning chamber provided so as to surround the first and second electrodes, and a fire-spread preventing unit provided in the burning chamber to prevent burning of the flammable refrigerant in the burning chamber from spreading outside the burning chamber.

19 Claims, 13 Drawing Sheets

REFRIGERATOR

CROSS-REFERENCE TO RELATED APPLICATIONS

This application is the National Phase of International Application No. PCT/JP02/09812 filed Sep. 24, 2002, which designated the U.S. and was published on Apr. 10, 2003 as International Publication No. WO 03/029733 A1, which is based upon and claims the benefit of priority from prior Japanese Patent Application No. 2001-303767 filed Sep. 28, 2001.

TECHNICAL FIELD

This invention relates to a refrigerator provided with a refrigerating cycle unit performing refrigeration by means of heat absorption due to change of a refrigerant from a liquid phase to a gaseous phase.

BACKGROUND ART

Nonflammable fleon has conventionally been used as a refrigerant for a refrigerating cycle unit of refrigerators. However, fleon has recently been found to result in destruction of an ozonosphere (ozone layer). Accordingly, arrangements and agreements have been made regarding reduction in an amount of fleon to be used and limitation in use of fleon. Isobutane has been examined as the refrigerant for the refrigerating cycle unit of the refrigerator instead of fleon.

However, isobutene, which is a flammable material comprising hydrocarbon as a base, has the following problems. Some types of refrigerators are provided with a deodorizer for eliminating odor component in cold air. One type of such deodorizers utilizes decomposition of odor component by ozone produced by high-voltage discharge between a pair of electrodes. In the case where this type of deodorizer is disposed in the refrigerator using isobutane as the refrigerant, the high-voltage discharge between the electrodes would ignite such that isobutane would catch fire or burning of isobutane would thermally damage the deodorizer or its peripheral components.

SUMMARY OF THE INVENTION

Therefore, an object of the present invention is to provide a refrigerator which comprises a deodorizer decomposing odor component by ozone produced by high-voltage discharge and a refrigerating cycle unit using a flammable refrigerant, wherein damage can be limited to the minimum even when the flammable refrigerant should leak out of the refrigerating cycle unit.

The present invention provides a refrigerator including a refrigerating cycle unit for refrigerating an atmosphere in the refrigerator by means of heat absorption due to change of a flammable refrigerant from a liquid phase to a gaseous phase, and a deodorizer having first and second electrodes discharging electricity upon application of high voltage thereto, producing ozone, characterized by a burning chamber provided so as to surround the first and second electrodes, and a fire-spread preventing unit provided in the burning chamber to prevent burning of the flammable refrigerant in the burning chamber from spreading outside the burning chamber.

In the above-described refrigerator, the burning of the refrigerant is limited to the inside of the burning chamber even when an abnormal condition causes the flammable refrigerant to leak out of the refrigerating cycle unit such that the refrigerant catches fire from the high-voltage discharge between the electrodes. Consequently, damage due to the burning of the flammable refrigerant can be prevented from being increased.

In a preferable form, the burning chamber includes a casing accommodating the first and second electrodes and has first and second windows located on a flow passage through which cold air is circulated in the refrigerator. Further, the first electrode is generally mesh-shaped and disposed in the casing so as to be opposed to the first window, and the second electrode is generally mesh-shaped and disposed in the casing so as to be opposed to the second window. Additionally, the wire netting covers the first and second windows. In the foregoing preferable form, cold air circulated in the interior of the refrigerator can flow between the first and second electrodes in the casing. Consequently, the odor component contained in the cold air can efficiently be decomposed by ozone produced by the discharge between the electrodes. Furthermore, the burning of the flammable refrigerant can be prevented from being spread by the simple wire netting covering the windows of the casing holding the first and second electrodes.

In another preferable form, the refrigerator is further characterized by a stopper for stopping an operation of the deodorizer upon occurrence of burning in the burning chamber. Consequently, damage due to the burning of the flammable refrigerant can be prevented from being spread even upon occurrence of the burning of the flammable refrigerant since the high-voltage discharge resulting in the burning is interrupted.

BEST MODE FOR ENFORCEMENT OF THE INVENTION

Figure 2:
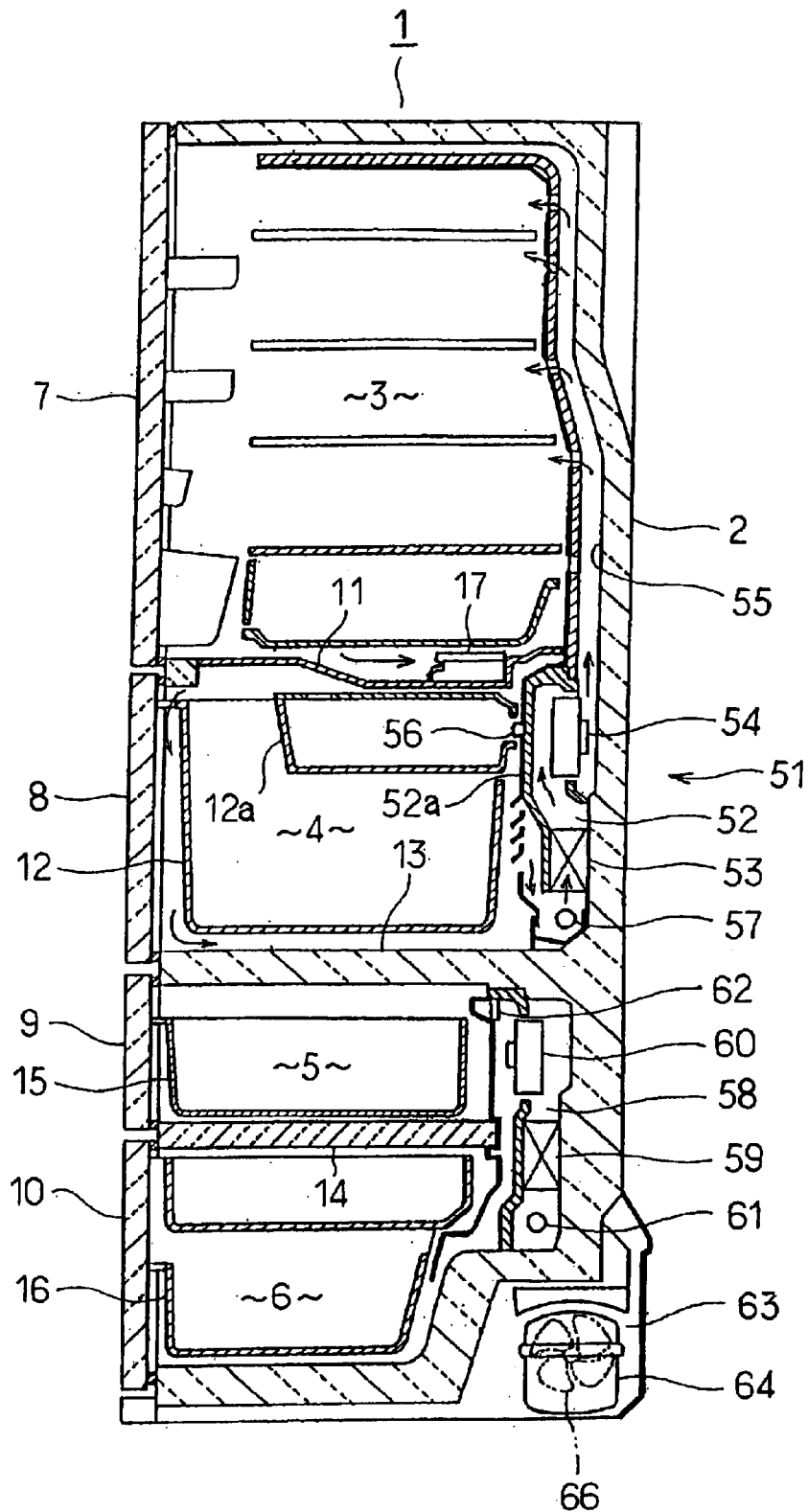
FIG. 2 is a longitudinally sectional side view of the refrigerator.

Three embodiments of the invention will be described with reference to the accompanying drawings. Referring first to FIG. 2, a bottom-freezer refrigerator of the first embodiment is shown. The refrigerator comprises a refrigerator body 1 formed into a vertically long rectangular heat-insulated box 2. A cold storage compartment 3, a vegetable compartment 4, a temperature-changeable compartment 5 and a freezing compartment 6 are defined in the heat-insulated box 2. An ice-making compartment is provided in juxtaposition with the temperature-changeable compartment 5 although not shown.

Figure 7:
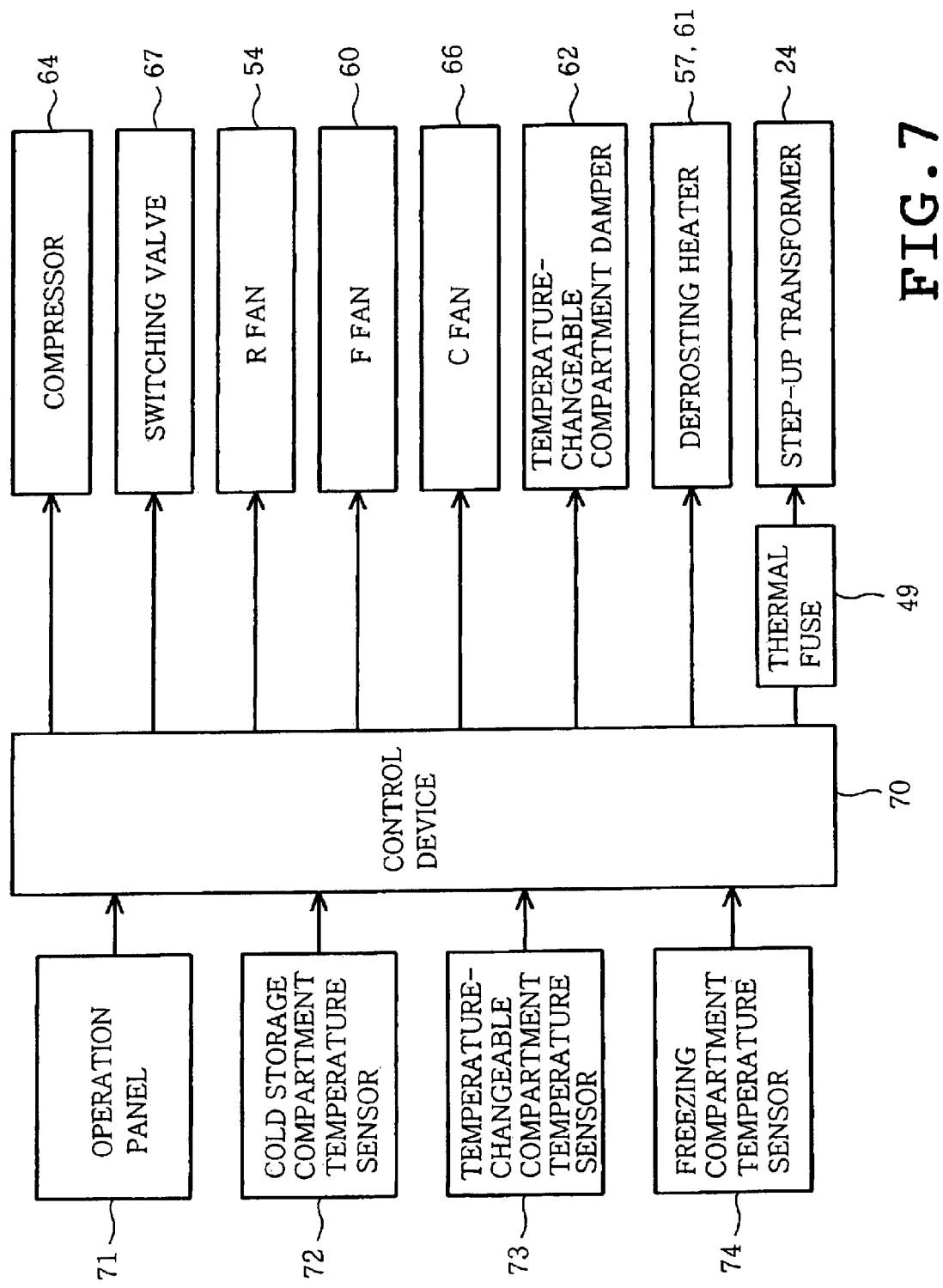
FIG. 7 is a block diagram showing an electrical arrangement of the refrigerator.

The heat-insulated box 2 has a front opening. The front opening of the cold storage compartment 3 is closed by a cold storage compartment door 7 hingedly mounted on the heat-insulated box 2. An operation panel 71 as shown in FIG. 7 is mounted on a front of the door 7. The front openings of the compartments 4 to 6 are closed by slidable doors 8 to 10 respectively. The front opening of the ice-making compartment is also closed by a door (not shown).

A partition plate 11 is provided between the cold storage and vegetable compartments 3 and 4 so as to define the upper cold storage compartment 3 and the lower vegetable compartment 4. A vegetable storage receptacle 12 is connected to a rear face of the door 8 and enclosed in the vegetable compartment 4 so as to be slidable forward and backward. An upper case 12*a* is mounted in an upper interior of the storage receptacle 12. A deodorizer 17 is mounted on a rear upper side of the partition plate 11 in the cold storage compartment 3. The deodorizer 17 will be described in detail later.

A heat-insulating partition wall 13 formed integrally with the heat-insulated box 2 partitions the upper vegetable compartment 4, and the lower temperature-changeable compartment 5 and ice-making compartment. Furthermore, a heat-insulating partition wall 14 partitions the upper temperature-changeable compartment 5 and ice-making compartment, and the lower freezing compartment 6. Additionally, a heat-insulating partition wall (not shown) partitions the temperature-changeable compartment 5 and the ice-making compartment. Thus, the temperature-changeable compartment 5 is isolated spatially and thermally from the other compartments.

A storage receptacle 15 is connected to a rear face of the door 9 and enclosed in the temperature-changeable compartment 5 so as to be slidable forward and backward. Also, a storage receptacle 16 is connected to a rear face of the door 10 and enclosed in the freezing compartment 6 so as to be slidable forward and backward.

A refrigerating cycle unit 51 is built in an inner part of the refrigerator body 1. More specifically, an evaporator chamber 52 for the cold storage or refrigerating compartment (hereinafter referred to as "R evaporator chamber") is defined by a partition wall 52*a* in a deep interior of the vegetable compartment 4. Furthermore, a cold air duct 55 is provided along a rear interior and an upper interior of the cold storage compartment 3 in the refrigerator body 1. The cold air duct 55 has a lower end connected to the R evaporator chamber 52.

An evaporator 53 for the cold storage or refrigerating compartment (hereinafter referred to as "R evaporator") is provided in the R evaporator chamber 52, and a blowing fan 54 for the cold storage compartment (hereinafter, referred to as "R fan") is provided above the evaporator 53. The partition wall 52*a* has an outlet 56 formed in a portion thereof located in front of the R fan 54. The outlet 56 has a front end opening located in the upper case 12*a*. The R fan 54 is of a variable speed type (for example, in a range of 1800 to 2400 rpm). Furthermore, a defrosting heater 57 is provided in the lower interior of the R evaporator chamber 52.

During drive of the R fan 54, cold air produced by the R evaporator 53 is supplied through the cold air duct 55 into the cold storage compartment 3 and simultaneously through the outlet 56 into the vegetable compartment 4. Thereafter, the cold air is caused to return into the R evaporator chamber 52, thus being circulated.

An evaporator chamber 58 for the freezing compartment (hereinafter "F evaporator chamber") is provided along rear interiors of the temperature-changeable compartment 5, ice-making compartment and lower freezing compartment 6. An evaporator 59 for the freezing compartment (hereinafter "F evaporator") is provided in the F evaporator chamber 58. A blowing fan 60 for the freezing compartment (hereinafter "F fan") is provided above the F evaporator 59 in the F evaporator chamber 58. The F fan 60 is of a variable speed drive type (for example, in a range of 1800 to 2400 rpm). Furthermore, a defrosting heater 61 is provided in the lower interior of the F evaporator chamber 58.

A damper 62 for the temperature-changeable compartment 5 is provided in a portion of a downstream or discharge side cold-air passage with respect to the F fan 60, the portion being connected to the temperature-changeable compartment. The damper 62 is controlled by a control device 70 (see FIG. 7) so as to be opened and closed.

When the F fan 60 is driven while the damper 62 is closed, cold air produced by the F evaporator 59 is supplied into the freezing compartment 6 and the ice-making compartment, thereafter being caused to return into the lower interior of the F evaporator chamber 58. Thus, the cold air is circulated. On the other hand, when the F fan 60 is driven while the damper 62 is closed completely or partly, cold air produced by the F evaporator 59 is supplied into the freezing compartment 6, the ice-making compartment, and the temperature-changeable compartment 5, thereafter being caused to return into the lower interior of the F evaporator chamber 58. Thus, the cold air is circulated.

A machine compartment 63 is defined in the lower rear of the refrigerator body 1. In the machine compartment 63 are provided a compressor 64 and a cooling fan 66 (hereinafter, "C fan") for cooling the compressor 64 and a condenser 65 (see FIG. 6). The compressor 64 is controlled by means of inverter control so that variable speed drive of the compressor (for example, in an operating frequency of the inverter ranging from 30 to 70 Hz) is achieved. The C fan 66 is also of a variable speed type (for example, in a range of 1800 to 2000 rpm).

Figure 6:
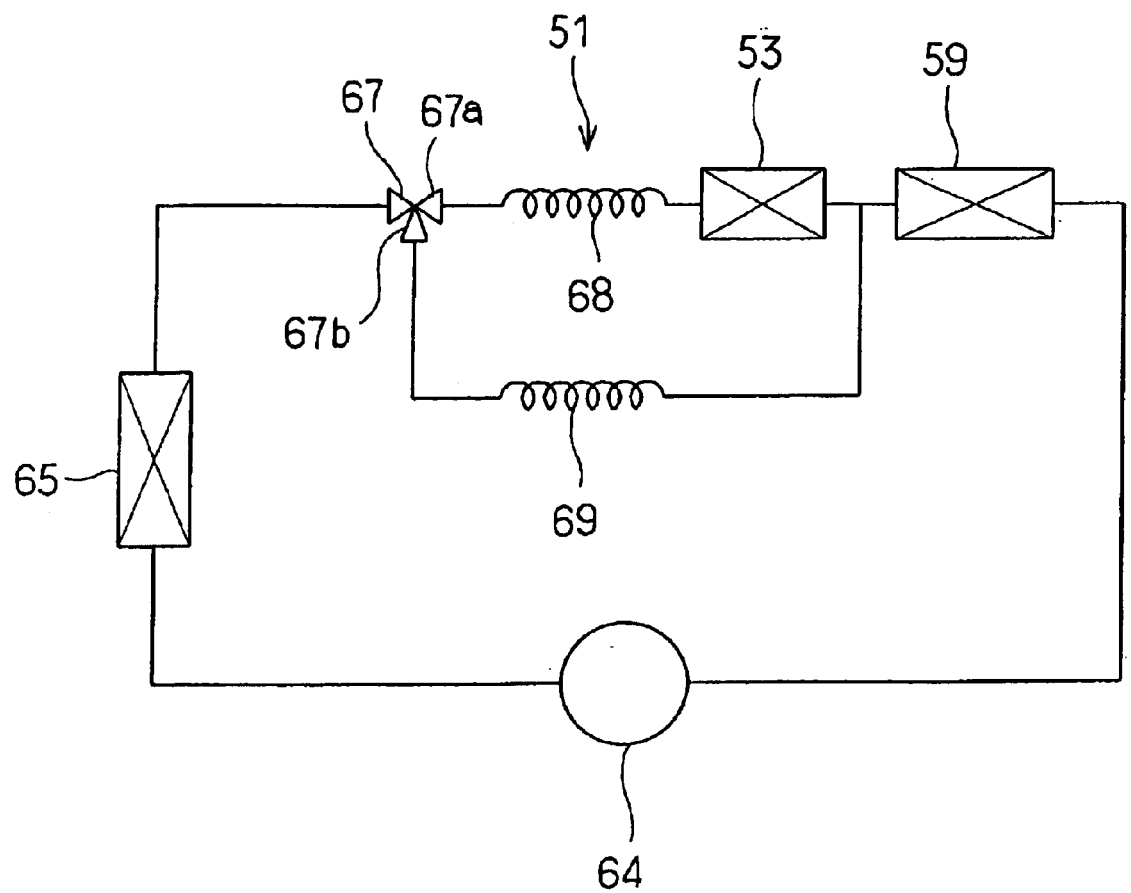
FIG. 6 is a schematic view of a refrigerating cycle unit.

Referring now to FIG. 6, a schematic arrangement of the refrigerating cycle unit 51 is shown. The refrigerating cycle unit 51 includes the compressor 64, the condenser 65, a switching valve 67 (three-way valve) serving as refrigerant flow passage switching means, a first capillary tube 68 connected to a first outlet 67*a* of the switching valve 67, the R evaporator 53 and the F evaporator 59, all of which are connected one to another sequentially by refrigerant pipes into a closed loop. A second capillary tube 69 is connected to a second outlet 67*b* of the switching valve 67 and further to the refrigerant pipe between the R and F evaporators 53 and 59. Thus, the second capillary tube 69 bypasses the first capillary tube 68 and the R evaporator 53.

When the switching valve 67 is switched to the first outlet 67*a* side or when the first outlet 67*a* is open, refrigerant having passed the condenser 65 and so on by drive of the compressor 64 is caused further to flow through the first capillary tube 68, R evaporator 53 and F evaporator 59 sequentially, thereafter returning to the compressor 64.

On the other hand, when the switching valve 67 is switched to the second outlet 67*b* side or when the second outlet 67b is open, refrigerant having passed the condenser 65 and so on by drive of the compressor 64 is caused further to flow through the second capillary tube 69 and F evaporator 59 in turn, thereafter returning to the compressor 64.

Isobutane, which is flammable, is used as a refrigerant circulated through the refrigerating cycle unit 51 in the embodiment.

The construction of the deodorizer 17 will now be described.

Figure 3:
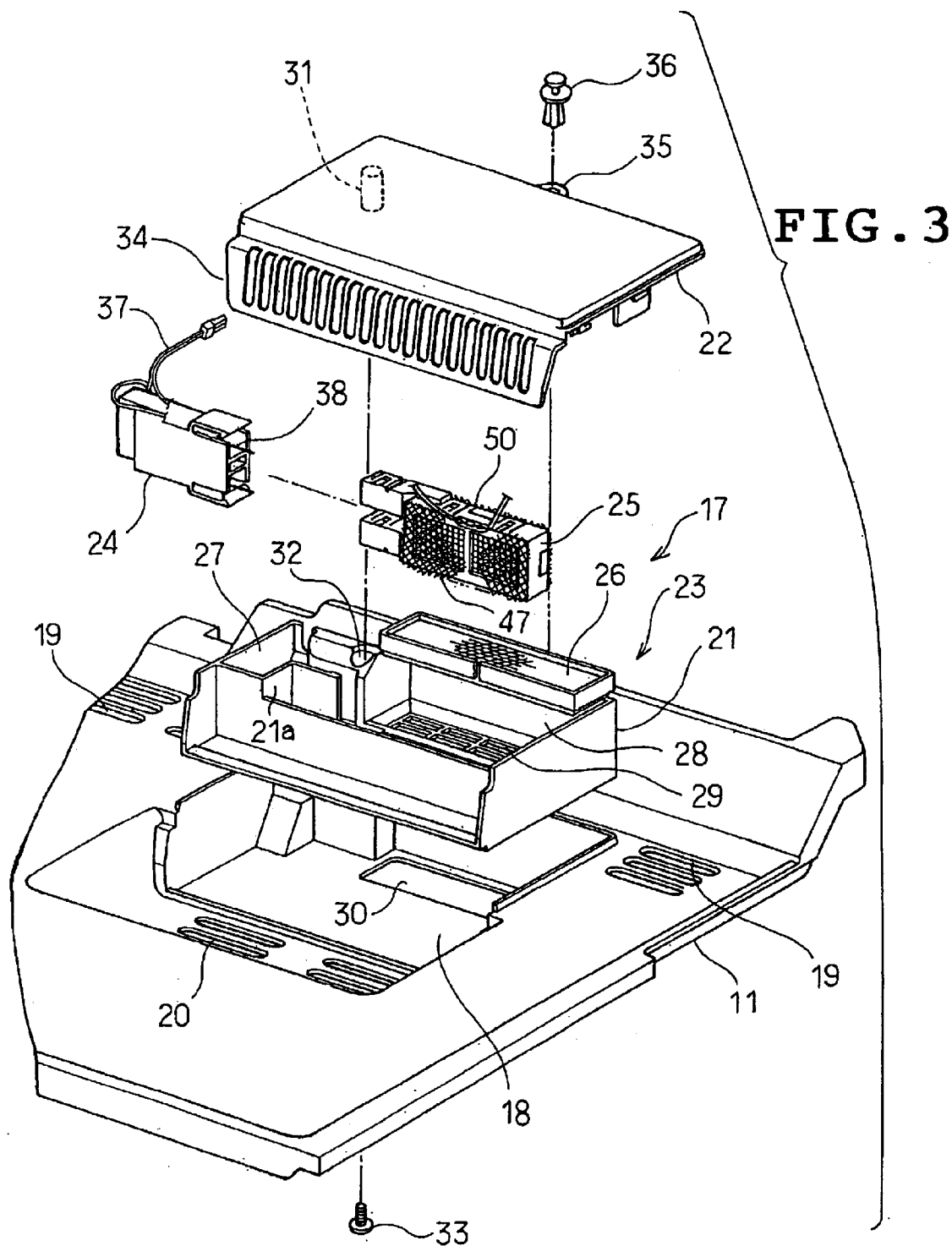
FIG. 3 is an exploded perspective view of a deodorizer used in the refrigerator.

FIG. 3 is an exploded perspective view of the deodorizer 17 together with the partition plate 11. In FIG. 3, the partition plate 11 is formed with a mount recess 18 to which the deodorizer 17 is attached. The partition plate 11 is further formed with a plurality of vent holes 19 at opposite sides of the mount recess 18 respectively so that circulated cold air is caused to flow directly from the cold storage compartment 3 into the vegetable compartment 4 without through the deodorizer 17.

The front bottom of the mount recess 18 is formed with a plurality of elongated drain holes 20 and the rear bottom thereof is formed with an opening 30. The drain holes 20 prevent water from entering the deodorizer 17 when the user accidentally spills the water in the refrigerator.

The deodorizer 17 includes a unit casing 23 further including a casing body 21 and a cover 22 covering an upper opening of the casing body, a step-up transformer 24, a photocatalyst unit 25 and an ozone-decomposing catalyst 26. The unit casing 23 is made from ABS, for example.

Figure 4:
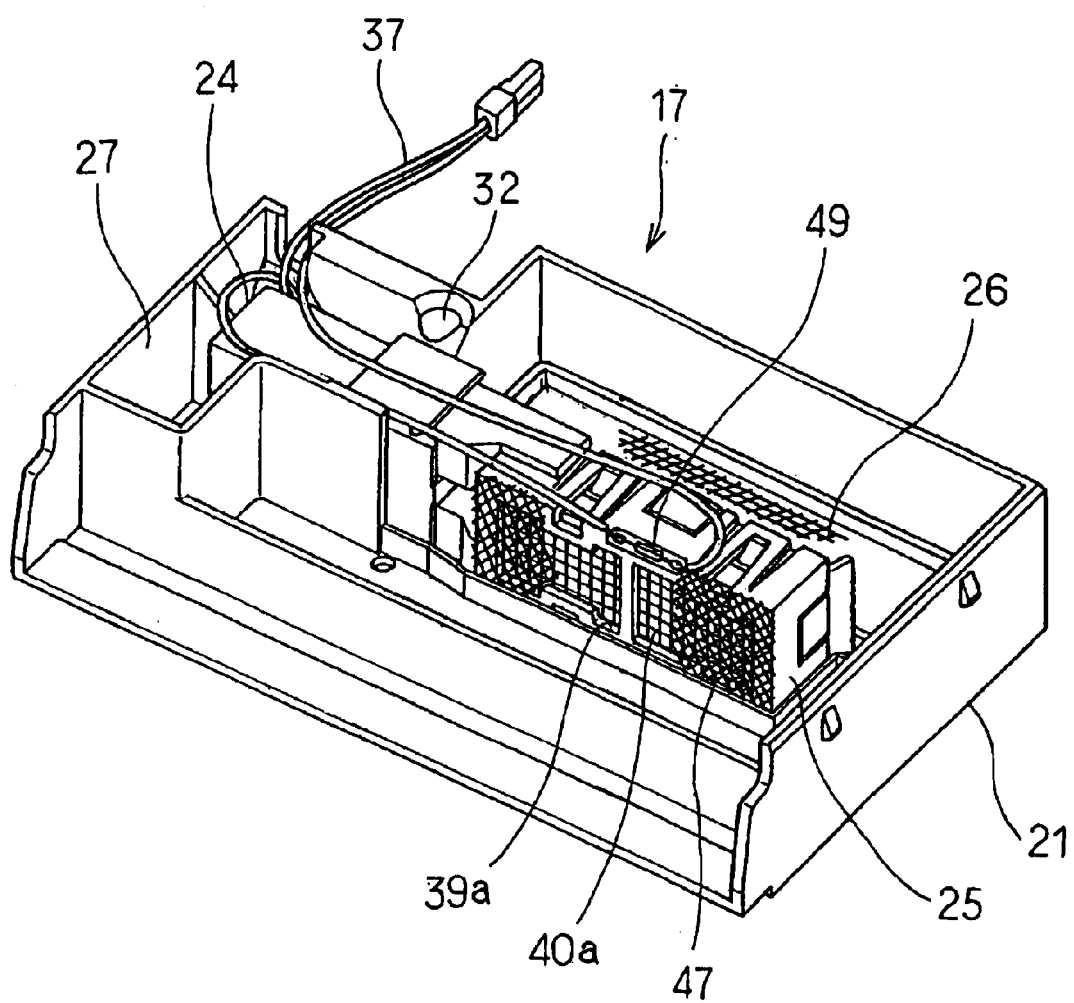
FIG. 4 is a perspective view of the deodorizer with a cover thereof eliminated.

The casing body 21 has an interior divided by a partition wall 21a into a transformer chamber 27 and a cold air passage 28, as shown in FIGS. 3 and 4. The step-up transformer 24 is disposed in the transformer chamber 27. The step-up transformer 24 includes a primary coil, a secondary coil and a magnetic core (none of which are shown) all enclosed by a synthetic resin by molding. The step-up transformer 24 steps up voltage of power supplied through an electric supply line 37 to a predetermined voltage, which is delivered from a secondary side terminal 38.

The photocatalyst unit 25 is disposed centrally in the cold air passage 28. The ozone-decomposing catalyst 26 is disposed in the rear of the photocatalyst unit 25. The casing body 21 has a number of vent holes 29 formed in a portion of the bottom thereof on which the ozone-decomposing catalyst 26 is disposed. The vent holes 29 are adapted to be opposed to the opening 30 when the deodorizer 17 is attached to the mount recess 18 of the partition plate 11.

The ozone-decomposing catalyst 26 includes a core which may be a ceramic honeycomb containing manganese oxide as a base or may be made by forming a metallic honeycomb into the shape of a generally rectangular plate, and a catalyst fixed to the core. Thus, a large area of contact of the catalyst 26 with ozone or odor component is ensured by the honeycomb structure, whereby the decomposing efficiency is improved. The ozone-decomposing catalyst 26 is disposed on the vent holes 29 so that air flows vertically through the honeycomb structure.

In mounting the cover 22 on the casing body 21, a boss 31 standing on the underside of the cover is inserted through a hole 32 formed in the casing body 21, and a screw 33 is screwed into the boss 31 from the underside of the partition plate 11. The cover 22 has a downwardly extending louver 34 integrally formed on the front end thereof. A lower end of the louver 34 is adapted to abut against the front end of the casing body 21 when the cover 22 is attached to the casing body. The louver 34 further prevents foreign matter from entering the unit casing 23.

The deodorizer 17 is attached to the mount recess 18 when an one-touch fastener is inserted from above into a hole 35 formed in a rear end of the cover 22 while the hole is in alignment with a hole (not shown) formed in a rear edge of the mount recess.

Figure 1:
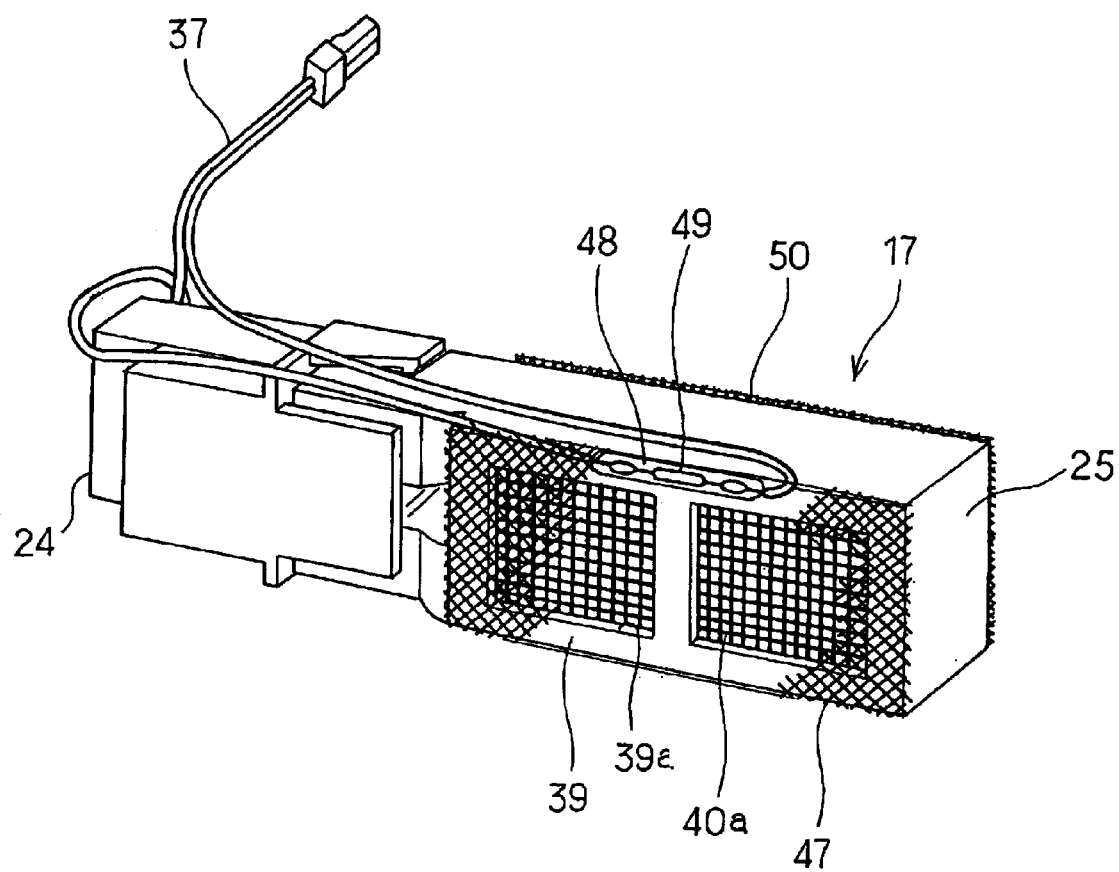
FIG. 1 is a perspective view of a photocatalyst unit employed in a refrigerator of a first embodiment in accordance with the present invention.
Figure 5:
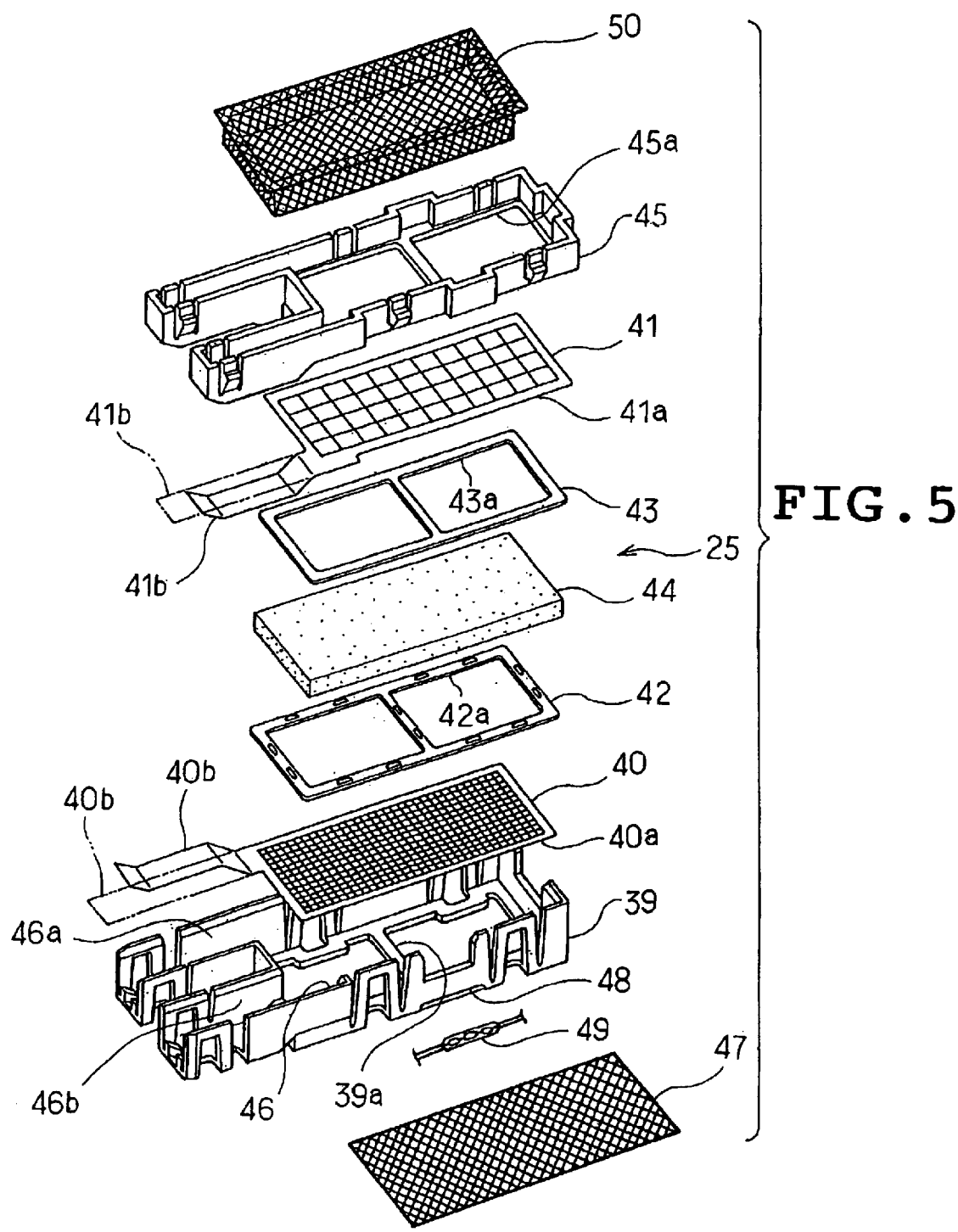
FIG. 5 is an exploded perspective view of the photocatalyst.

The photocatalyst unit 25 will now be described in detail with reference to FIGS. 1 and 5. The foregoing step-up transformer 24 is connected to the photocatalyst unit 25 by means of engagement to supply a predetermined high voltage to the unit. The photocatalyst unit 25 comprises a first case 39, a first electrode 40 and a second electrode 41 both accommodated in the first case, spacers 42 and 43 serving as buffers, a photocatalyst module 44 and a second case 45 attached to the first case. The first electrode 40 includes a mesh electrode portion 40a and a terminal portion 40b. The second electrode 41 includes a mesh electrode portion 41a and a terminal portion 41b. The mesh electrode portion 41a of the second electrode 41 has larger meshes than the mesh electrode portion 40a of the first electrode 40.

The spacers 42 and 43 are both made from a nonflammable silicon rubber. Each of the spacers 42 and 43 is formed into the shape of a frame and has two windows 42a or 43a. The photocatalyst module 44 comprises a rectangular plate-shaped core made from a porous ceramic such as alumina or silica and having a surface to which a photocatalytic material such as titanium oxide is applied, the photocatalytic material being dried or fired. The first case 39 has an accommodation recess 46 and a pair of terminal disposition portions 46a and 46b both communicating with the storage recess. The accommodation recess 46 accommodates the mesh electrode portion 40a of the first electrode 44, spacer 42, photocatalyst module 44, spacer 43, mesh electrode portion 41a of the second electrode 41 sequentially in this order. The terminal portions 40b and 41b of the first and second electrodes 40 and 41 are disposed in the terminal disposition portions 46a and 46b respectively.

The accommodation recess 46 has a bottom formed with windows 39a (serving as first windows) corresponding to the windows 42a and 43a respectively. The first case 39 has an outer face to which a wire netting 47 (serving as a fire-spread preventing unit) is attached so as to cover the window 39a. When having been accommodated in the accommodation recess 46, the mesh electrode portion 40a of the first electrode 40 is opposed to the wire netting 47 with the window 39a being positioned therebetween.

The first case 39 further has an attachment recess 48 formed in an outer edge thereof. A thermal fuse 49 (serving as a stopper) is attached to the attachment recess 48. The thermal fuse 49 is connected in series to the primary side of the step-up transformer 24. The thermal fuse 49 is brought into contact with an inside of the wire netting 47 so that heat is transferred from the wire netting to the thermal fuse. When the temperature of the thermal fuse 49 is increased to, for example, 70° C., the thermal fuse 49 is melted to thereby cut off power supply to the primary side of the step-up transformer 24.

The second case 45 is fitted into the accommodation recess 46 and terminal disposition portions 46a and 46b of the first case 39 after the first electrode 40, spacer 42, photocatalyst module 44, spacer 43 and second electrode 41 have been accommodated in the accommodation recess 46 and terminal disposition portions 46a and 46b. Thus, the photocatalyst unit 25 is constructed.

The second case 45 is formed with a window 45a serving as a second window. A wire netting 50 serving as a fire-spread preventing unit is attached to an outer face of the second case 45 so as to cover the window 45*a*. The mesh electrode portion 41*a* of the second electrode 41 is opposed to the wire netting 50 with the window the window 45*a* being positioned therebetween.

Each of the wire nettings 47 and 50 is made of an austenitic stainless steel with high ozone resistance, preferably a wire material with a wire diameter of 0.18 mm, such as SUS304 or SUS316, the wire material being formed into a mesh (60 meshes per square centimeter). A space defined by the first and second cases 39 and 45 and wire nettings 47 and 50 serves as a burning chamber. The burning chamber is provided so that if discharge between the first and second electrodes 40 and 41 should cause isobutane leaking from the refrigerating cycle unit 51 to burn, the burning is limited to an interior of the burning chamber, or in order that the burning of isobutane may be prevented from spreading out of the burning chamber. For this purpose, the capacity of the burning chamber and a flow rate of cold air flowing through the burning chamber are set so that isobutane contained in the cold air flowing through the interior of the burning chamber is intermittently caused to burn.

A secondary terminal 38 of the step-up transformer 24 is electrically connected to the first and second electrodes 40 and 41 of the photocatalyst unit 25 when the step-up transformer is attached to the photocatalyst unit. Consequently, the step-up transformer 24 can supply high voltage to the photocatalyst unit 25.

FIG. 7 is a block diagram showing an electrical arrangement of the refrigerator body 1. In FIG. 7, to the microcomputer-based control device 70 are supplied signals from an operation panel 71, cold storage compartment temperature sensor 72, temperature-changeable compartment temperature sensor 73, freezing compartment temperature sensor 74, etc. Based on the signals from the operation panel 71 and sensors 72 to 74, the control device 70 controls the compressor 64, switching valve 67, R fan 54, F fan 60, C fan 66, temperature-changeable compartment damper 62, defrosting heaters 57 and 61, step-up transformer 24 of the deodorizer 17, etc. so that these are energized. In this case, the control device 70 controls the switching valve 67 to switch the latter, thereby alternately carrying out a cold storage compartment cooling mode in which the refrigerant is caused to flow into the R evaporator 53 so that atmospheres in the cold storage and vegetable compartments 3 and 4 are mainly cooled, and a freezing compartment cooling mode in which the refrigerant is caused to flow only into the F evaporator 59 so that the atmosphere in the freezing compartment 6 and the atmosphere in the temperature-changeable compartment 5, if necessary, are cooled.

Predetermined temperature ranges are set for the cold storage compartment 3, vegetable compartment 4, temperature-changeable compartment 5 and freezing compartment 6 respectively. Based on temperatures detected by the respective temperature sensors 72 to 74, the control device 70 controls the switching valve 67, temperature-changeable compartment damper 62, fans 54, 60 and 66, and compressor 64 so that temperatures in the compartments 4 to 6 are maintained in the respective set ranges. For example, an upper limit (or ON temperature) of the set temperature range of the freezing compartment 6 and ice-making compartment is set at −18° C. and a lower limit (or OFF temperature) is set at −21° C. Furthermore, an upper limit (ON temperature) of the set temperature range is set at 5° C. and a lower limit (OFF temperature) is set at 2° C.

The operation of the refrigerator will now be described. When the control device 70 starts the refrigerating operation for the cold storage and vegetable compartments 3 and 4, the refrigerant discharged by the compressor 64 is supplied into the R evaporator 53. Furthermore, the R fan 54 and deodorizer 17 are operated. As a result, part of cold air produced in the R evaporator 52 is discharged from the cold air outlet 56 into the vegetable compartment 4 as shown by arrows in FIG. 2, thereafter being returned to the R evaporator chamber 52. The remainder of the cold air produced in the R evaporator 52 is discharged into the cold storage compartment 3 while flowing upward through the cold air duct 55. Most of the cold air discharged into the cold storage compartment 3 directly flows into the vegetable compartment 4 through the vent holes 29 of the partition plate 11. Part of the cold air discharged into the cold storage compartment 3 and not passing through the vent holes 29 passes through the deodorizer 17, thereafter returning through the vegetable compartment 4 into the R evaporator chamber 52.

The cold air firstly flows into the cold air passage 28 in the deodorizer 17, then passing through the photocatalyst unit 25 and ozone-decomposing catalyst 26 in turn. In the photocatalyst unit 25, the step-up transformer 24 periodically applies the impulse voltage of 8.8 kV across the first and second electrodes 40 and 41, whereby a corona discharge is caused between the mesh electrodes 40*a* and 41*a*. The corona discharge has such a level that electrons move along surfaces of the mesh electrodes 40*a* and 41*a*. This level does not deprive of strength of the electrodes. Accordingly, the first and second electrodes can be used continuously. The surfaces of the mesh electrodes 40*a* and 41*a* become a plasma state during delivery of electrons, thereby producing ultraviolet rays (wavelength of 380 nm or below) and ozone.

A high voltage of 8.8 kV is applied between the first and second electrodes 40 and 41 according to the distance therebetween. Accordingly, there is a possibility that current may leak to the wire nettings 47 and 50 located near the mesh electrodes 40*a* and 41*a*. However, since the wire nettings 47 and 50 are electrically separated in the embodiment, a leak current can be prevented from flowing from the first electrode 40 through the wire nettings 47 and 50 to the second electrode 41.

When the ultraviolet rays produced with the corona discharge between the first and second electrodes 40 and 41 are irradiated onto the photocatalyst module 44, light energy of the ultraviolet rays activates titanium oxide, which decomposes, by photocatalytic action, odor components such as ammonia contained in the cold air or ethylene gas reducing freshness of food. Since the photocatalyst module 44 is disposed between the mesh electrode portions 40*a* and 41*a* particularly in the embodiment, non-directional ultraviolet rays emitted with the corona discharge effectively acts on the photocatalyst module 44.

Furthermore, the ozone produced by the corona discharge passes the ozone-decomposing catalyst 26 together with the cold air. In this case, the ozone is decomposed such that active oxygen is produced. Odor components of amine system contained in the cold air and odor components such as ammonia are decomposed by the oxidizing force of the active oxygen. More specifically, the ethylene gas contained in the cold air is decomposed by the photocatalyst module 44 and the odor components such as of amine system contained in the cold air, whereas odor components such as ammonia are decomposed both by the photocatalyst module 44 and by the ozone decomposing catalyst 26. The cold air which has been deodorized by the deodorizer 17 flows through the vent holes 29 of the unit case 23 and the opening 30 of the partition plate 11 into the vegetable compartment 4, further returning to the R evaporator chamber 52. Thus, the atmospheres in the respective cold storage and vegetable compartments 3 and 4 can be cooled by the cold air produced in the R evaporator chamber 52 while the odor components contained in the cold air can be decomposed.

The refrigerating cycle unit 51 is composed of a plurality of components coupled to one another by refrigerant pipes. Accordingly, when a failure occurs in a junction between each component and the refrigerant pipe, there is a possibility that flammable isobutane filling the interior may leak. The density of isobutane contained in the cold air is gradually increased upon leakage thereof. With this, the density of isobutane contained in the atmosphere around the photocatalyst unit 25 is also increased. In the embodiment, however, the distance between the mesh electrode portions 40a and 41a of the photocatalyst unit 25 is set at 8.5 mm and the applied voltage is set at 8.8 kV so that corona discharge with small energy is produced between the mesh electrode portions. Consequently, isobutane can be prevented from burning even when the density of isobutane contained in the atmosphere around the photocatalyst unit 25 is increased.

However, a part of each mesh electrode portion 40a, 41a is bent such that the distance between the electrodes is reduced, a discharge voltage is increased or an electrically conductive foreign matter is placed between the electrode portions. In each case, an abnormal discharge or arc discharge is produced between the electrode portions 40a and 41a. The arc discharge indicates that an air insulation layer between the mesh electrode portions 40a and 41a has been broken. The arc discharge has a large energy since a large current flows. Accordingly, there is a possibility that isobutane would burn when the density of isobutane is increased. Since the deodorizer 17 is disposed in the cold air passage particularly in the embodiment, isobutane which is a flammable gas is continuously supplied to the discharge source. Accordingly, the temperature in the refrigerator may excessively be increased even when the refrigerator has an arrangement that the step-up transformer 24 is cut off by the thermal fuse 49.

Figure 8:
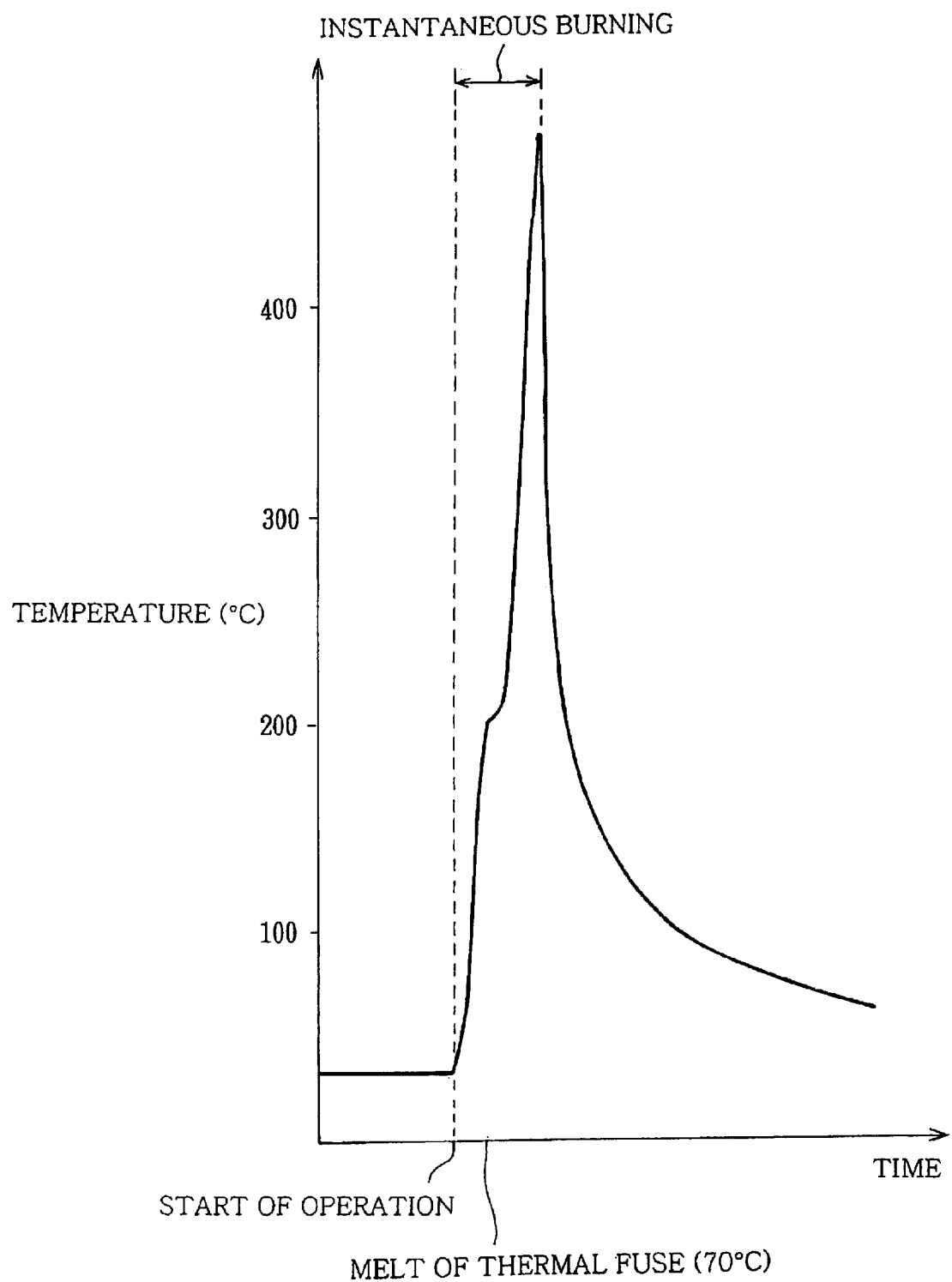
FIG. 8 is a graph showing changes in a temperature in a burning chamber with a wire netting eliminated.

FIG. 8 shows experimental results concerning temperature changes in the photocatalyst unit 25 in the case where arc discharge was caused in the atmosphere of isobutane with gas density of 4.2%/vol so that the isobutane burned. In the experiment, the wire nettings 47 and 50 were eliminated from the photocatalyst unit 25 of the deodorizer 17. The resultant construction corresponded with a conventional construction. As shown in FIG. 8, a large quantity of isobutane instantaneously burned upon start of operation (start of discharge) and accordingly, the temperature in the photocatalyst unit 25 was rapidly increased. The temperature of the thermal fuse 49 reached 70° C. 30 seconds after start of operation. As a result, the thermal fuse 49 was melted to cut off the step-up transformer 24. Thereafter, the temperature in the photocatalyst unit 25 further continued the rapid increase. Isobutane burned out when the temperature in the photocatalyst unit 25 had reached 485° C. The temperature in the photocatalyst unit 25 was rapidly reduced after isobutane had burned out. In this case, the temperature of the unit case 32 of the deodorizer 17 was increased such that the unit case was deformed and then emitted smoke. The deodorizer thus has a problem of safety.

Figure 9:
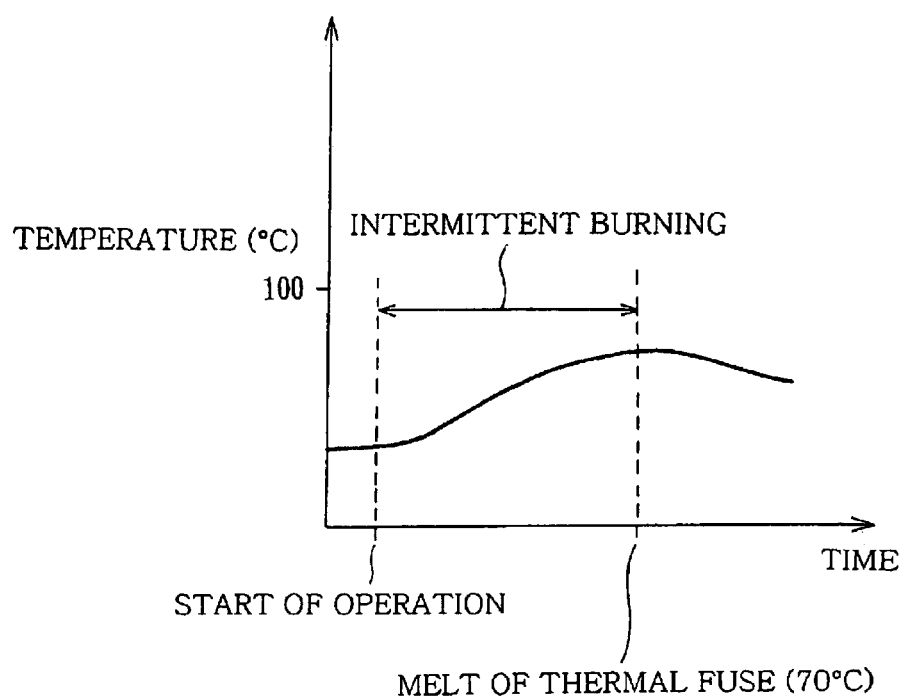
FIG. 9 is a graph showing changes in the temperature in the burning chamber with the wire netting attached.

On the other hand, FIG. 9 shows experimental results concerning temperature changes in the photocatalyst unit 25 of the deodorizer 17 in the embodiment in the case where arc discharge was caused in the atmosphere of isobutane with gas density of 4.2%/vol so that the isobutane burned. As shown in FIG. 9, a temperature increase in the photocatalyst unit 25 was gentle even when arc discharge between the mesh electrode portions 40a and 41a burned isobutane. The reason for this is that the windows 39a and 45a of the cases 39 and 45 of the photocatalyst unit 25 were covered with the wire nettings 47 and 50 so that a burning chamber is defined so that isobutane intermittently burned but did not spread outside the burning chamber.

The temperature in the photocatalyst unit 25 reached 70° C. five minutes and 20 seconds after start of the operation. At that time, the thermal fuse 49 melted to cut off the step-up transformer 24. Thereafter, burning was not continued although isobutane was supplied such that the temperature in the photocatalyst unit 25 was gradually reduced. No deformation could be found in the unit case 23 of the deodorizer 17.

The experimental data shows that burning occurs at intervals of 3 or 4 seconds in the photocatalyst unit 25 and that an amount of cold air passing through the photocatalyst unit 25 is restrained by the wire nettings 47 and 50, whereupon a sufficient burning interval can be ensured.

In the foregoing embodiment, the windows 39a and 45a of the cases 39 and 45 of the photocatalyst unit 25 are covered with the wire nettings 47 and 50 respectively so that the burning chamber is defined. Accordingly, even if the arc discharge between the mesh electrodes 40a and 41a should cause isobutane to burn, the burning can be confined to the interior of the burning chamber. Since a temperature increase becomes gentle in the photocatalyst unit 25, the cutoff by the thermal fuse 49 can follow the temperature increase in the photocatalyst unit.

Furthermore, since the burning of isobutane is prevented from spreading outside the photocatalyst unit 25, the case 23 composing the deodorizer 17 and peripheral components can be prevented from breakage. Moreover, the foregoing effects can be achieved by a simple arrangement of covering the windows 39a and 45a of the cases 39 and 45 with the respective wire nettings 47 and 50.

Furthermore, each wire netting can be prevented from corrosion by ozone since it is made from stainless steel. Additionally, the wire nettings 47 and 50 are electrically separated from the first and second electrodes 40 and 41 respectively. Consequently, current can be prevented from leaking through the wire nettings 47 and 50.

Figure 10:
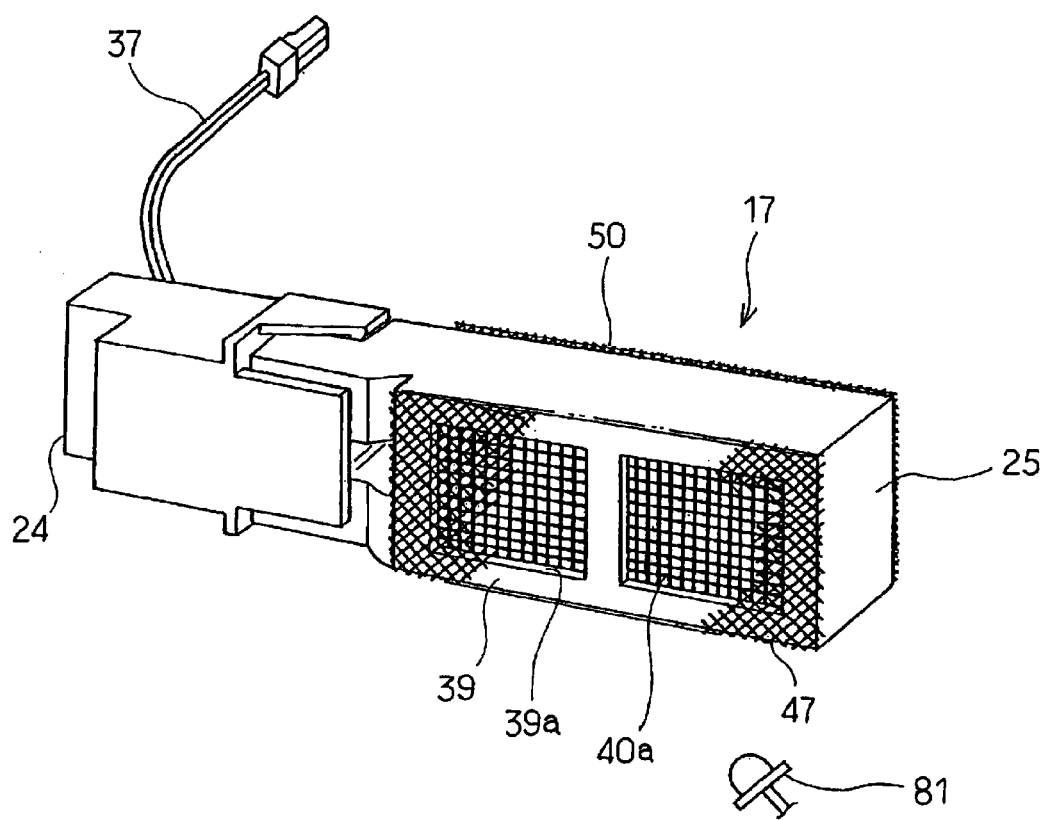
FIG. 10 is a view similar to FIG. 1, showing the photocatalyst unit employed in the refrigerator of a second embodiment in accordance with the invention.
Figure 11:
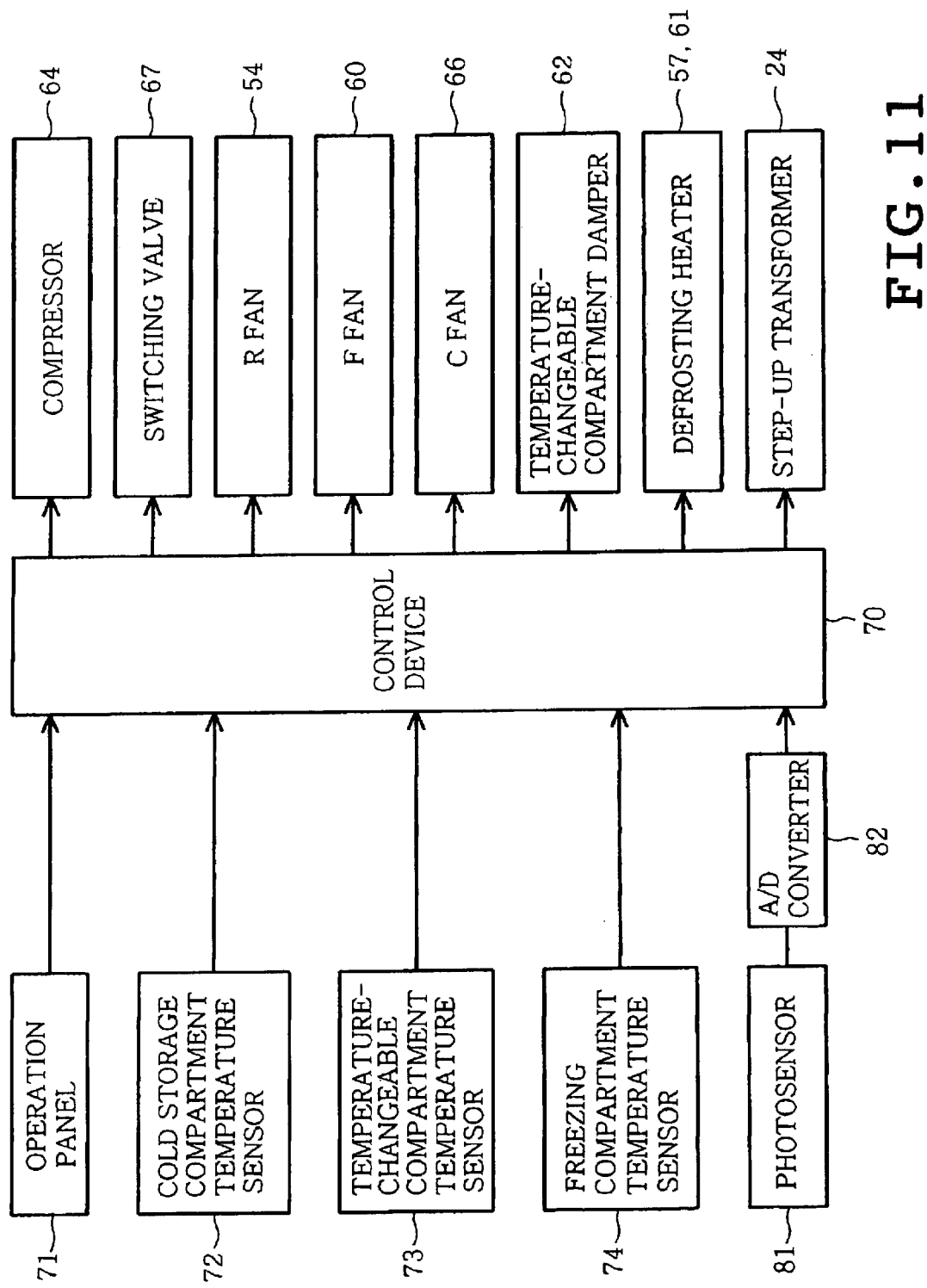
FIG. 11 is a view similar to FIG. 7.
Figure 12:
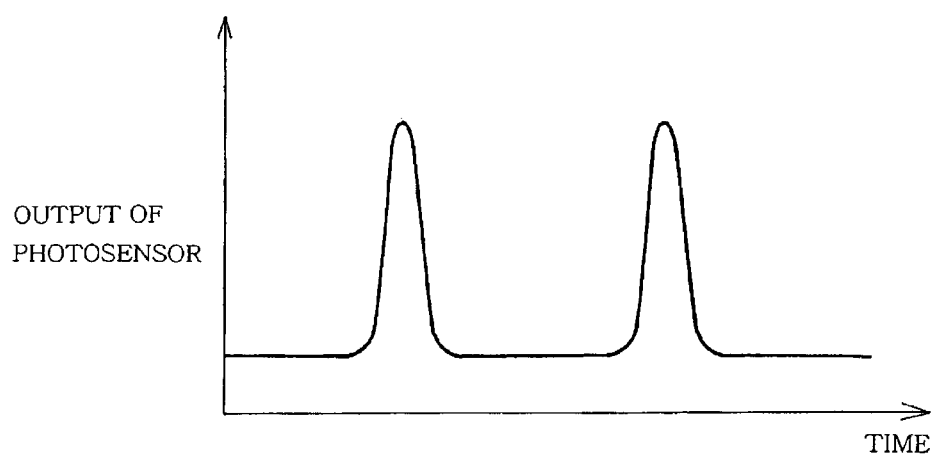
FIG. 12 is a graph showing changes in an amount of light detected by the photosensor.

FIGS. 10 to 12 illustrate a second embodiment of the invention. Differences of the second embodiment from the first embodiment will be described. Identical or similar parts are labeled by the same reference symbols as those in the first embodiment. The second embodiment is characterized by a photosensor detecting occurrence of burning in the photocatalyst unit 25.

More specifically, as shown in FIG. 10, a photosensor 81 is provided near the photocatalyst unit 25. When burning occurs in the photocatalyst unit 25, light emitting with the burning is detected by the photosensor 81. Ultraviolet rays due to the corona discharge are usually emitted from the photocatalyst unit 25. The used photosensor 81 has such a light detecting characteristic that it does not detect ultraviolet rays. Furthermore, the deodorizer 17 is not provided with the thermal fuse 49 used in the first embodiment.

FIG. 11 is a block diagram showing an electrical arrangement of the refrigerator of the second embodiment. Output from the photosensor 81 is converted to a corresponding digital signal by an A/D converter 82. The digital signal is supplied to the control device 70. Based on the digital signal from the A/D converter 82, the control device 70 determines an amount of light detected by the photosensor 81. The control device 70 interrupts energization of the step-up transformer 24 when a change in an amount of light detected by the photosensor 81 shows a predetermined pattern.

FIG. 12 shows changes in an amount of light detected by the photosensor 81. When the arc discharge causes isobutane in the photocatalyst unit 25 to burn, an amount of light detected by the photosensor 81 is intermittently increased since the burning intermittently takes place. When the change in an amount of light detected by the photosensor 81 shows such an intermittent pattern, the control device 70 interrupts energization of the step-up transformer 24. Consequently, the deodorizer 17 is interrupted, so that continuous burning of isobutane is prevented even if isobutane contained in cold air is continuously supplied into the photocatalyst unit 25.

In the second embodiment, the burning of isobutane in the photocatalyst unit 25 is quickly detected by the photosensor 81, and the deodorizer 17 is interrupted at once. Consequently, damage can be restrained to the minimum.

Figure 13:
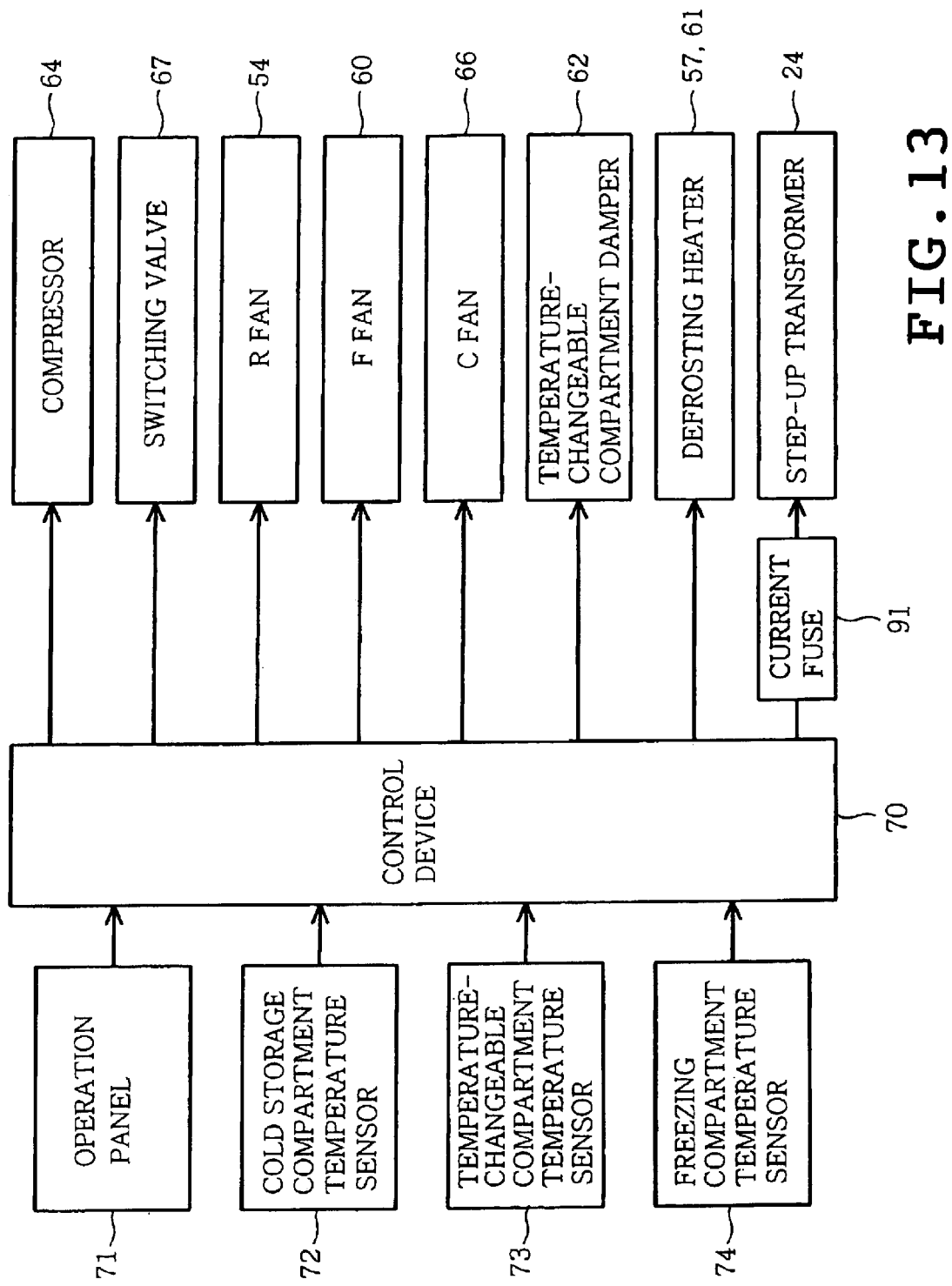
FIG. 13 is a view similar to FIG. 7, showing an electrical arrangement of the refrigerator of a third embodiment in accordance with the invention.

FIG. 13 illustrates a third embodiment of the invention. Differences of the third embodiment from the first embodiment will be described. In the third embodiment, the control device 70 supplies power through a current fuse 91 (serving as a stopper) to the step-up transformer 24. The current fuse 91 is set so as not to cut off power in response to an amount of power upon occurrence of corona discharge between the first and second electrodes 40 and 41 but so as to cut off power in response to an amount of power upon occurrence of arc discharge between the first and second electrodes 40 and 41.

More specifically, power supply to the step-up transformer 24 is interrupted upon occurrence of arc discharge between the first and second electrodes 40 and 41 irrespective of leak of isobutane from the refrigerating cycle unit 51. Consequently, the burning of isobutane due to arc discharge can be prevented.

The present invention should not be limited to the foregoing embodiments and can be modified or expanded as follows.

The thermal fuse may be eliminated in the first embodiment. In this arrangement, the burning of isobutane in the photocatalyst unit 25 is intermittently continued. However, since the burning volume is small, an excessive temperature increase can be restrained and accordingly, safety can be ensured.

Arrangement of each embodiment may be combined together.

INDUSTRIAL APPLICABILITY

As described above, the present invention can be utilized as a refrigerator provided with a refrigerating cycle unit and taking care of earth environment by employment of an inflammable non-fleon refrigerant as cooling refrigerant.

What is claimed is:

1. A refrigerator including a refrigerating cycle unit for refrigerating an atmosphere in the refrigerator by means of heat absorption due to change of a flammable refrigerant from a liquid phase to a gaseous phase, and a deodorizer having first and second electrodes discharging electricity upon application of high voltage thereto, producing ozone, characterized by:
    a burning chamber provided so as to surround the first and second electrodes; and
    a fire-spread preventing unit provided in the burning chamber to prevent burning of the flammable refrigerant in the burning chamber from spreading outside the burning chamber.

2. A refrigerator according to claim 1, characterized in that the first and second electrodes generate ultraviolet rays by means of high-voltage discharge and further characterized by a photocatalyst held between the first and second electrodes so as to perform a photocatalytic reaction upon irradiation of ultraviolet rays thereon.

3. A refrigerator according to claim 1, characterized in that the fire-spread preventing unit comprises a wire netting.

4. A refrigerator according to claim 3, characterized in that the wire netting is made of a stainless steel.

5. A refrigerator according to claim 3, characterized in that:
    the burning chamber includes a casing accommodating the first and second electrodes and has first and second windows located on a flow passage through which cold air is circulated in the refrigerator;
    the first electrode is generally mesh-shaped and disposed in the casing so as to be opposed to the first window;
    the second electrode is generally mesh-shaped and disposed in the casing so as to be opposed to the second window; and
    the wire netting covers the first and second windows.

6. A refrigerator according to claim 4, characterized in that:
    the burning chamber includes a casing accommodating the first and second electrodes and has first and second windows located on a flow passage through which cold air is circulated in the refrigerator;
    the first electrode is generally mesh-shaped and disposed in the casing so as to be opposed to the first window;
    the second electrode is generally mesh-shaped and disposed in the casing so as to be opposed to the second window; and
    the wire netting covers the first and second windows.

7. A refrigerator according to claim 5, characterized in that the wire netting is electrically insulated from the first and second electrodes.

8. A refrigerator according to claim 6, characterized in that the wire netting is electrically insulated from the first and second electrodes.

9. A refrigerator according to claim 1, further characterized by a stopper for stopping an operation of the deodorizer upon occurrence of burning in the burning chamber.

10. A refrigerator according to claim 9, characterized in that the stopper comprises a thermal fuse disposed in the burning chamber so as to be fused when a temperature thereof increases to or above a predetermined temperature, thereby cutting off the deodorizer.

11. A refrigerator according to claim 10, characterized in that the thermal fuse is disposed so that heat is transferred from the wire netting thereto.

12. A refrigerator according to claim 10, characterized by a step-up transformer supplying high voltage to the deodorizer and in that the thermal fuse is connected in series to a primary side of the step-up transformer.

13. A refrigerator according to claim 11, characterized by a step-up transformer supplying high voltage to the deodorizer and in that the thermal fuse is connected in series to a primary side of the step-up transformer.

14. A refrigerator according to claim 10, characterized in that burning of the flammable refrigerant contained in the cold air circulated through the burning chamber is intermittently caused in the burning chamber.

15. A refrigerator according to claim 11, characterized in that burning of the flammable refrigerant contained in the cold air circulated through the burning chamber is intermittently caused in the burning chamber.

16. A refrigerator according to claim 12, characterized in that burning of the flammable refrigerant contained in the cold air circulated through the burning chamber is intermittently caused in the burning chamber.

17. A refrigerator according to claim 13, characterized in that burning of the flammable refrigerant contained in the cold air circulated through the burning chamber is intermittently caused in the burning chamber.

18. A refrigerator according to claim 9, characterized in that the stopper is provided with a photosensor for detecting luminescence occurring with burning in the burning chamber, and the stopper stops the operation of the deodorizer when the photosensor has detected the luminescence.

19. A refrigerator according to claim 1, further characterized by a current fuse for cutting off the deodorizer when current supplied into the deodorizer increases to or above a predetermined value.

* * * * *